United States Patent [19]

Magerlein

[11] 4,065,631
[45] Dec. 27, 1977

[54] 17-PHENYL-18,19,20-TRINOR-CIS-4,5-DIDEHYDRO-PGF$_{1\beta}$ COMPOUNDS

[75] Inventor: Barney J. Magerlein, Portage, Mich.

[73] Assignee: The Upjohn Company, Kalamazoo, Mich.

[21] Appl. No.: 741,246

[22] Filed: Nov. 12, 1976

Related U.S. Application Data

[62] Division of Ser. No. 580,747, May 27, 1975, Pat. No. 4,032,561.

[51] Int. Cl.$^2$ ............................................. C07C 69/76
[52] U.S. Cl. ................................... 560/55; 260/520 B
[58] Field of Search ....................... 260/473 A, 520 B

[56] References Cited

FOREIGN PATENT DOCUMENTS

| 7,301,094 | 7/1973 | Netherlands | 260/473 |
| 7,306,461 | 11/1973 | Netherlands | 260/473 |
| 7,501,560 | 8/1975 | Netherlands | 260/473 |

Primary Examiner—Paul J. Killos
Attorney, Agent, or Firm—Robert A. Armitage

[57] ABSTRACT

The disclosure includes novel compounds which differ from the known prostaglandins PGF$_{2\alpha}$, PGF$_{2\beta}$, PGE$_2$, PGA$_2$, and PGB$_2$ in that the carbon-carbon double bond in the carboxyl-terminated chain of the novel compounds is in the 4,5-position rather than in the 5,6-position, and in that there is a phenyl or substituted phenyl group in the other chain of the novel compounds. These novel compounds are useful for a variety of pharmacological purposes, including abortion, labor induction, and reduction of gastric secretion.

7 Claims, No Drawings

17-PHENYL-18,19,20-TRINOR-CIS-4,5-DIDEHYDRO-PGF$_{1\beta}$ COMPOUNDS

The present application is a divisional application of Ser. No. 580,747, filed May 27, 1975, now issued as U.S. Pat. No. 4,032,561, on June 28, 1977.

The present invention relates to prostaglandin analogs for which the essential material constituting a disclosure therefor is incorporated by reference here from U.S. Pat. No. 4,032,561, issued June 28, 1977.

I claim:

1. An optically active compound of the formula:

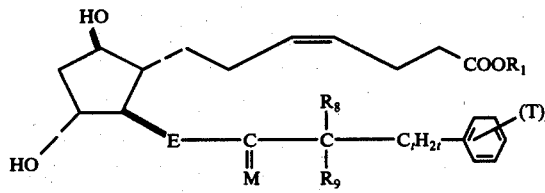

or a racemic form of that compound and the enantiomer thereof, wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive;

wherein M is

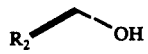

or

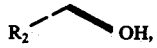

wherein $R_2$ is hydrogen, methyl, or ethyl;

wherein E is trans—CH=CH— or —CH$_2$CH$_2$—;

wherein $R_8$ is hydrogen and $R_9$ is hydrogen, methyl, or fluoro, or wherein $R_8$ and $R_9$ are both methyl or both fluoro, with the proviso that neither of $R_8$ and $R_9$ is methyl when $R_2$ is methyl or ethyl;

wherein $C_tH_{2t}$ represents a valence bond or alkylene of one to 9 carbon atoms, inclusive, with one to 6 carbon atoms, inclusive, between —CR$_8$R$_9$— and the ring; and wherein T is alkyl of one to 4 carbon atoms, inclusive, fluoro, chloro, trifluoromethyl, or —OR$_3$, wherein $R_3$ is alkyl of one to 4 carbon atoms, inclusive and wherein s is zero, one, 2, or 3 with the proviso that not more than 2 T's are other than alkyl; including alkanoates of 2 to 8 carbon atoms, inclusive, and pharmacologically acceptable salts thereof when $R_1$ is hydrogen.

2. An optically active compound according to claim 1, wherein E is trans—CH=CH—, $R_1$ is hydrogen, methyl, or ethyl, M is

s is zero or one, T when present is chloro, fluoro, or trifluoromethyl, $R_8$ and $R_9$ are methyl, or $R_8$ is hydrogen and $R_9$ is fluoro, and $C_tH_{2t}$ is —CH$_2$— or —CH$_2$CH$_2$—, and pharmacologically acceptable salts thereof when $R_1$ is hydrogen.

3. An optically active compound according to claim 1, wherein E is trans—CH=CH—, $R_1$ is hydrogen, methyl, or ethyl, M is

wherein $R_2$ is hydrogen or methyl, s is zero or one, T when present is chloro, fluoro, or trifluoromethyl, $R_8$ and $R_9$ are hydrogen, and $C_tH_{2t}$ is —CH$_2$— or —CH$_2$CH$_2$—, and pharmacologically acceptable salts thereof when $R_1$ is hydrogen.

4. cis-4,5-Didehydro-17-phenyl-18,19,20-trinor-PGF$_{1\beta}$, a compound according to claim 3, wherein $R_1$, $R_2$, $R_8$, and $R_9$ are hydrogen, s is zero, and $C_tH_{2t}$ is —CH$_2$—.

5. cis-4,5-Didehydro-17-phenyl-18,19,20-trinor-PGF$_{1\beta}$, methyl ester, a compound according to claim 3, wherein $R_1$ is methyl, $R_2$, $R_8$, and $R_9$ are hydrogen, s is zero, and $C_tH_{2t}$ is —CH$_2$—.

6. cis-4,5-Didehydro-15-methyl-17-phenyl-18,19,20-trinor-PGF$_{1\beta}$, a compound according to claim 3, wherein $R_1$, $R_8$, and $R_9$ are hydrogen, $R_2$ is methyl, s is zero, and $C_tH_{2t}$ is —CH$_2$—.

7. cis-4,5-Didehydro-15-methyl-17-phenyl-18,19,20-trinor-PGF$_{1\beta}$, methyl ester, a compound according to claim 3, wherein $R_1$ and $R_2$ are methyl, $R_8$ and $R_9$ are hydrogen, s is zero, and $C_tH_{2t}$ is —CH$_2$—.

* * * * *